United States Patent
Kwon

(10) Patent No.: US 11,007,229 B2
(45) Date of Patent: May 18, 2021

(54) METHOD FOR INDUCING TRANSDIFFERENTIATION OF FIBROBLASTS INTO CHONDROCYTES

(71) Applicant: HANYANG DIGITEK CO., LTD.

(72) Inventor: Hyuck Joon Kwon, Seoul (KR)

(73) Assignee: YOUTH BIO GLOBAL CO., LTD, Seoul (KR)

( * ) Notice: Subject to any disclaimer, the term of this patent is extended or adjusted under 35 U.S.C. 154(b) by 317 days.

(21) Appl. No.: 16/071,117

(22) PCT Filed: Jan. 2, 2017

(86) PCT No.: PCT/KR2017/000031
§ 371 (c)(1),
(2) Date: Jul. 19, 2018

(87) PCT Pub. No.: WO2017/131353
PCT Pub. Date: Aug. 3, 2017

(65) Prior Publication Data
US 2019/0175659 A1   Jun. 13, 2019

(30) Foreign Application Priority Data

Jan. 29, 2016 (KR) .................. 10-2016-0011238

(51) Int. Cl.
| | |
|---|---|
| *A61K 35/32* | (2015.01) |
| *A61P 19/02* | (2006.01) |
| *A61P 19/04* | (2006.01) |
| *A61P 19/08* | (2006.01) |
| *C12N 5/077* | (2010.01) |

(52) U.S. Cl.
CPC .............. *A61K 35/32* (2013.01); *A61P 19/02* (2018.01); *A61P 19/04* (2018.01); *A61P 19/08* (2018.01); *C12N 5/0655* (2013.01); *C12N 5/0656* (2013.01)

(58) Field of Classification Search
None
See application file for complete search history.

(56) References Cited

U.S. PATENT DOCUMENTS

2013/0089908 A1   4/2013   Creecy

FOREIGN PATENT DOCUMENTS

| KR | 1020050044849 | 5/2005 |
|---|---|---|
| KR | 1020120029367 | 3/2012 |
| KR | 1020140137882 | 12/2014 |
| KR | 1016531970000 | 8/2016 |

OTHER PUBLICATIONS

Tew, et al. (2008) "Cellular methods in cartilage research: Primary human chondrocytes in culture and chondrogenesis in human bone marrow stem cells", Methods, 45: 2-9. (Year: 2008).*
Kwon, et al. (Dec. 22, 2016) "Electrical stimulation drives chondrogenesis of mesenchymal stem cells in the absence of exogenous growth factors", Nature, Scientific Reports, 6: Article 39302, 13 pages. (Year: 2016).*
Ikeda, T., et al., "The Combination of SOX5, SOX6, and SOX9 (the SOX Trio) Provides Signals Sufficient for Induction of Permanent Cartilage" Arthritis & Rheumatism, 50(11): 3561-3573, 2004 (13 pages total).
Hiramatsu, K. et al., "Generation of hyaline cartilaginous tissue from mouse adult dermal fibroblast culture by defined factors" Journal of Clinical Investigation, 121(2): 640-657, 2011 (19 pages total).
Outani, H. et al., "Direct Induction of Chondrogenic Cells from Human Dermal Fibroblast Culture by Defined Factors" PLoS ONE, 8(10) :e77365, Oct. 2013 (12 pages total).
Kim, H.J., et al., "Is Continuous Treatment with Transforming Growth Factor-Beta Necessary to Induce Chondrogenic Differentiation in Mesenchymal Stem Cells?" Cells Tissues Organs, 190, 1-10, 2009 (11 pages total).
Agley et al., "Human skeletal muscle fibroblasts, but not myogenic cells, readily undergo adipogenic differentiation" J. Cell Biol., 126(24): 5610-5625, 2013 (16 pages total).
Ge et al., "Selection of Cell Source for Ligament Tissue Engineering" Cell Transplantation, 14: 573-583, 2005 (11 pages total).
Lim, Hyun-Pil et al., "Attachment and Proliferation of Human Gingival Fibroblasts on the Implant Abutment Materials" Journal of Korean Academy of Prosthodontics, vol. 44, No. 1, pp. 112-123, 2006 (English Language translation of Abstract) (12 pages total).
Eckhard Alt et al. "Fibroblasts share mesenchymal phenotypes with stem cells, but lack their differentiation and colony-forming potential" Biol. Cell (2011) 103, 197-208.

* cited by examiner

*Primary Examiner* — Robert M Kelly
(74) *Attorney, Agent, or Firm* — Mayer & Williams, PC; Stuart H. Mayer

(57) ABSTRACT

The present invention relates to a method for transdifferentiating cells. The present invention provides a method for transdifferentiating fibroblasts into chondrocytes, comprising: forming a micromass of fibroblasts by culturing fibroblasts in a high density; and applying an electrical stimulation such as a current or magnetic field to the micromass of fibroblasts while culturing the micromass of fibroblasts in a culture medium not containing growth factors.

6 Claims, 3 Drawing Sheets

Specification includes a Sequence Listing.

Control  ES

METHOD FOR INDUCING TRANSDIFFERENTIATION OF FIBROBLASTS INTO CHONDROCYTES

TECHNICAL FIELD

The present invention relates to a method for inducing transdifferentiation of cells, and more specifically, to a method for inducing transdifferentiation of fibroblasts into chondrocytes.

BACKGROUND ART

Cartilage is a very unique tissue in the human body and it has no blood vessel, no nerve, and does not regenerate well. Genes that induce the overexpression of three types of proteins (i.e., SOX5, SOX6 and SOX9), which are transcription factors known to be important for cartilage differentiation, were introduced into skin cells and directly transdifferentiated into chondrocytes successfully, but the characteristics of the cells as fibroblasts were not completely removed and they thus appear to be fibrous cartilage rather than glassy cartilage (Ikeda, T., et al., *Arthritis Rheum.* 50: 3561-3573, 2004). As a result of the development of reprogramming technology that introduces four types of transcription factors into differentiated cells and artificially transforms them into stem cells, studies on tissue regeneration using iPSCs (i.e., stem cells prepared by reprogramming) have been actively carried out. However, the tissue regeneration using iPSCs have disadvantages in that the tissue regeneration process is a complex process that has to undergo two steps (i.e., a reprogramming process and a differentiation process of differentiating cells into desired cells) and that there is a risk that undifferentiated cells may cause cancer when differentiating iPSCs. Recently, in order to overcome the disadvantages of tissue regeneration using iPSCs, the importance of the development of transdifferentiation technology that differentiates already-differentiated cells into desired cells has been raised. In particular, skin cells can easily be collected from a patient's body and are very easy to grow, and thus studies have been actively carried out to regenerate tissues by transdifferentiating using skin cells. It has been reported that genes that induce overexpression of C-Myc and Klf4 (i.e., two types of transcription factors that cause induction into artificially induced stem cells) and Sox9 protein (i.e., a transcription factor that induces cartilage differentiation) were introduced into mouse skin cells and successfully led to the direct transdifferentiation into glassy cartilage (Hiramatsu, K. et al., *Journal of Clinical Investigation*, 121: 640-657, 2011). Additionally, it has been reported that the introduction genes that induce overexpression of two genes encoding transcription factors that cause induction into artificially induced stem cells (C-Myc and Klf4) and a gene encoding Sox9 protein which is a transcription factor that induces cartilage differentiation) into human skin cells enables direct transdifferentiation into glassy cartilage (Outani, H. et al., *PLoS ONE*, 8:e77365, 2013).

DISCLOSURE OF THE INVENTION

Technical Problem

However, the aforementioned induction of transdifferentiation by the introduction of a gene has a problem in that the efficiency of gene introduction is low and the gene is inserted into the chromosome of host cells and destroys other genes thereby causing side effects such as cancer development. There is no efficient method for transdifferentiating fibroblasts into chondrocytes other than the method of genetic engineering.

The present invention has been made to solve the above-mentioned problems, and an object of the present invention is to provide a more efficient method for inducing transdifferentiation of fibroblasts into chondrocytes. However, the object is for illustrative purpose only and the scope of the present invention is not limited thereto.

Technical Solution

According to an aspect of the present invention, the provided is a method for transdifferentiating fibroblasts into chondrocytes, which includes forming a micromass of fibroblasts by culturing fibroblasts in a high density; and applying an electrical stimulation to the micromass of fibroblasts while culturing the micromass of fibroblasts in a culture medium not containing growth factors.

According to still another aspect of the present invention, the provided is transdifferentiated chondrocyte produced by the method.

According to yet another aspect of the present invention, a pharmaceutical composition for treating a condition related to cartilage damage comprising the transdifferentiated chondrocyte as an active ingredient.

Advantageous Effects

As described above, according to an embodiment of the present invention, the effect of transdifferentiating fibroblasts into chondrocytes can be realized more efficiently than conventional methods. Of course, the scope of the present invention is not limited by these effects.

MODE FOR CARRYING OUT THE INVENTION

Definition of Terms

Figure 1:
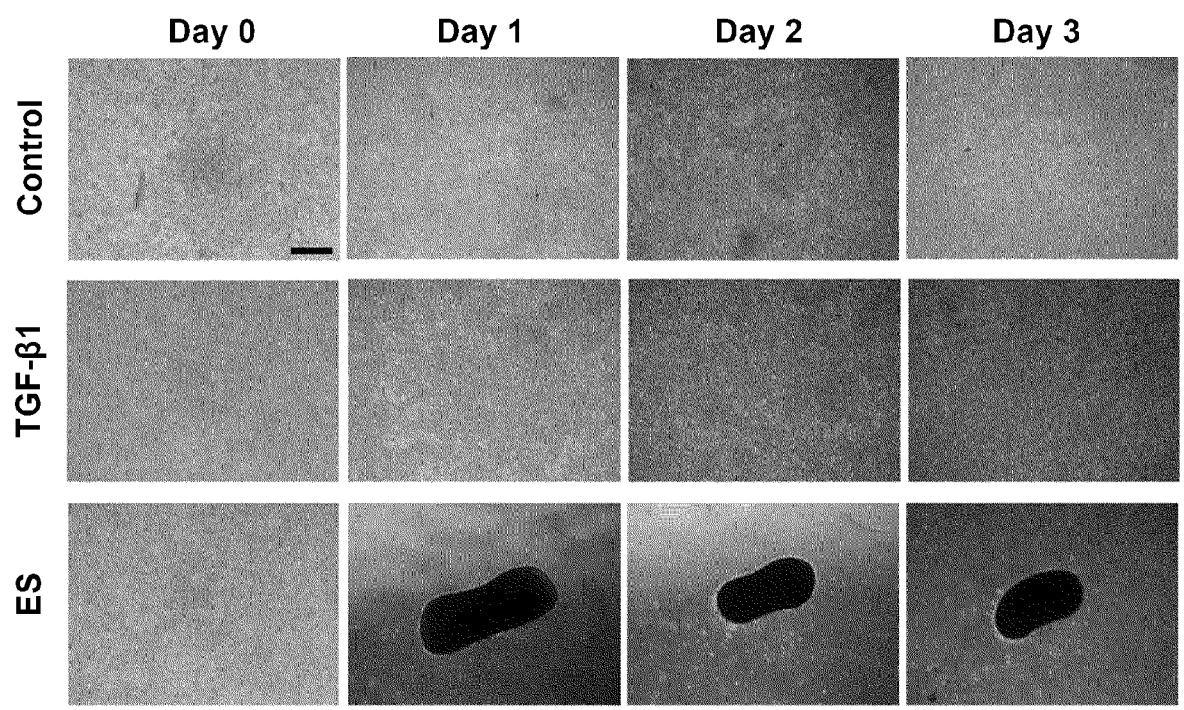
FIG. 1 shows images illustrating the morphological changes in fibroblasts of adults during electrical stimulation according to Comparative Example 1 (no treatment), Comparative Example 2 (treatment with TGF-β1), and an embodiment of the present invention.

The terms used in this specification are defined as follows.

As used herein, the term "fibroblast" refers to a cell type that synthesizes an extracellular matrix and collagen (i.e., the structural framework of animal tissue), and it plays an important role in wound healing and is the most common cell in animal connective tissue.

As used herein, the term "connective tissue" refers to one of the four types of biological tissues that support, connect, or separate other tissues and organs in the body.

The activity of melanocytes in the skin lead to formation of pigments or melanin, and as used herein, the term "skin cell" refers to skin-constituting cells including melanocytes. The melanocytes absorb part of the ultraviolet rays in the sunlight that may be harmful. They also have DNA repair enzymes that help to restore UV damage, and people who have a deficiency with the genes that make these enzymes are highly likely to get skin cancer. Skin is known as the largest organ in the human body. On the surface, the skin occupies the largest surface of all organs by covering the body. Moreover, even in weight, the skin weighs more than any organ in the body, which accounts for about 15% of the total body weight. For average adult humans, the surface area of the skin is 1.5 $m^2$ to 2.0 $m^2$, and most of the thickness is 2 mm to 3 mm. On average, 6.5 $cm^2$ (one square inch) of the skin has 650 sweat glands, 20 blood vessels, 60,000 melanocytes, and more than 1,000 nerve endings.

As used herein, the term "cartilage" refers to one which forms part of the joint in most cases, except the process that it is developed. When a relatively less movement is needed, the cartilage shows a shape of a cartilage joint that connects the bones by the cartilage. Meanwhile, it is based on the fact that when a lot of exercises are needed, the joint cartilage covering the synovial joints where two cartilaginous surfaces are in contact with each other through the synovial fluid has a very low coefficient of friction and can thus move with little friction. Cartilage consists of chondrocytes and fibrous matrix. With regard to the minimum conditions for growth factor to promote the differentiation into the cartilage, the formation of tissue-engineered new cartilage may be achieved more economically if sufficient cartilage can be formed by the initial one to two doses of transforming growth factor-beta (TGF-β). With regard to the degree of cartilage formation, continuous administration in proportion to the number of TGF-β administration is needed (Kim, H. J., et al., *Cells Tissues Organs*, 190: 1-10, 2009).

As used herein, the term "chondrocyte" refers to a unique cell found in healthy cartilage and it functions to create and maintain cartilaginous matrices mainly consisting of collagen and proteoglycan. As the maternal cells to be transformed into cartilage proliferate, the number of mesenchymal cells per unit area increases, resulting in a dense structure and the cells inside the maternal body gradually show halophilism, and these cells are called chondroblasts. Chondroblasts form collagen fibers and matrices, and as the cells in the center continue to form more substrates, the chondroblasts differentiate into chondrocytes as they separate from each other. Chondrocytes are in the lacunae and contain large amounts of lipids and glycogen. Chondrocytes and the lacunae vary in shape depending on their location in cartilage. The chondrocytes in the subchondral membrane are arranged so that their long axis are parallel to the surface (i.e., arranged flat like fibroblasts). The cells in the deep layer of cartilage and their lacunae are generally in a round shape.

As used herein, the term "micromass" refers to a three-dimensional cell culture formed by culturing cells at a high density without an exogenous growth factor or three-dimensional scaffold. Unlike normal monolayer cultures, when cells are dripped and cultured at a high density (about $1\times10^6$ cells/mL to about $1\times10^8$ cells/mL) so as not to contact the walls of a culture dish, the cells at the bottom attach to the culture dish and the cells are three-dimensionally laminated and cultured as a whole, and these three-dimensional laminated cells formed in this way are called micromass.

As used herein, the term "transdifferentiation" refers to the process of inducing the conversion between mature (differentiated) cells with totally different types of cells in higher organisms. Unlike the process of reprogramming with induced pluripotent stem cells (iPSCs) and redifferentiating them into desired cells, the transdifferentiation shows a difference in that it induces the direct conversion to the desired cell without going through the stage of iPSCs. Currently, direct transdifferentiation is recognized for its potential use in disease modeling, development of new drugs, etc., it is expected to be applied to gene therapy, regenerative medicine, etc. in the future.

As used herein, the term "type I collagen" is the most abundant protein among the collagen proteins that form a neutrophil fiber bundle known as collagen fibers, and includes α1 encoded by the COL1A1 gene and α2 encoded by the COLA1A2 gene. Type 1 collagen is mainly found in tissues such as tendons and skin.

As used herein, the term "type II collagen" refers to a collagen highly distributed in cartilage, about 20% of which is in the shape of chondroitin, and mutations in the COL2A gene that encodes this gene can be a cause of diseases such as congenital spondylodiphyseal dysplasia.

As used herein, the term "aggrecan (AGC)" refers to a human protein that is encoded by cartilage-specific proteoglycan nuclear protein (PS PCP) or ACAN gene, which is known as chondroitin sulfate proteoglycan 1. The aggrecan protein is a member of lecticans (chondroitin sulfate proteoglycans), an integral part of the extracellular matrix in cartilage tissue and sustains compression in cartilage.

As used herein, the term "SOX9" refers to a human transcription factor protein encoded by SOX-9 gene. SOX9 recognizes the CCTTGAG sequence along with the DNA binding protein of the high motility group-box (HMG-box) and regulate the transcription of steroidal gene 1 and anti-mullerian hormone (AMH) genes during the differentiation of cartilage.

As used herein, the term "TGF-β" refers to a protein that plays an important role in tissue fibrosis and remodeling of the extracellular matrix (ECM), upregulates CCN2/CTGF, PAI-1, and TIMP-1 as well as COL1A2, and the activity of the COL1A2 promoter of skin fibroblasts varies according to TGF-β stimulation.

MODES FOR CARRYING OUT THE INVENTION

Hereinafter, the present invention will be described in more detail.

According to still another aspect of the present invention, the provided is a method for transdifferentiating fibroblasts into chondrocytes comprising: forming a micromass of fibroblasts by culturing fibroblasts in a high density; and applying an electrical stimulation to the micromass of fibroblasts while culturing the micromass of fibroblasts in a culture medium not containing growth factors.

The method may be performed in vitro.

In the method, the fibroblasts may be derived from tendon, ligament, muscle, skin, cornea, periodontal tissue, cartilage, bone, blood vessel, small intestine, large intestine, or intervertebral disc.

In the method, the fibroblasts may be seeded at a concentration of $1\times10^6$ cells/mL to $1\times10^8$ cells/mL.

In the method, the electrical stimulation may be applied by direct current or alternating current.

In the method, the electrical stimulation may have an electric field strength of 1 V/cm to 100 V/cm, 1 V/cm to 50 V/cm, 1 V/cm to 20 V/cm, 1 V/cm to 10 V/cm, or 3 V/cm to 7 V/cm, and the electrical stimulation may be applied at a cycle of 1 to 100 stimuli per second, 1 to 50 stimuli per second, 1 to 20 stimuli per second, 1 to 10 stimuli per second, or 3 to 7 stimuli per second; for 1 ms to 30 ms per stimulus, for 1 ms to 20 ms per stimulus, for 1 ms to 15 ms per stimulus, or for 5 ms to 10 ms per stimulus; and the electrical stimulation may be performed for 12 hours to 10 days, for 1 to 8 days, or 2 to 5 days.

According to still another aspect of the present invention, the provided is a transdifferentiated chondrocyte produced by the method for transdifferentiating fibroblasts into chondrocytes.

According to still another aspect of the present invention, there is provided a pharmaceutical composition for treating a condition related to cartilage damage comprising the transdifferentiated chondrocyte as an active ingredient. Since the active ingredient of the pharmaceutical composition is the transdifferentiated chondrocyte, it may also be called a cellular therapeutic agent.

In the pharmaceutical composition, the condition related to cartilage damage may be semilunar cartilage injury, triangular fibrocartilage complex injury, severe cartilage damage or partial cartilage damage by repeated trauma, osteoarthritis (degenerative arthritis), or rheumatoid arthritis.

The cellular therapeutic agent or pharmaceutical composition according to an embodiment may be administered through any common route of administration as long as they can arrive at the target tissue. For example, such a route may include parenteral administration (e.g., intraperitoneal, intravenous, intramuscular, subcutaneous, intrasynovial, and intra-articular administration), and in particular, intraarticular administration to the target lesion is most preferred, but the administration route is not limited thereto.

The cellular therapeutic agent or pharmaceutical composition according to an embodiment may be formulated in a suitable form together with a pharmaceutically acceptable carrier. Examples of the pharmaceutically acceptable carrier may include carriers for parenteral administration (e.g., water, suitable oils, saline, aqueous glucose, glycols, etc.), etc. and the cellular therapeutic agent or pharmaceutical composition may further contain a stabilizers and a preservative. Examples of a suitable stabilizer include antioxidants such as sodium bisulfite, sodium sulfite, and ascorbic acid. Examples of a suitable preservative include benzalkonium chloride, methyl- or propyl-paraben and chlorobutanol. Additionally, the composition for treating cells according to the present invention may appropriately contain a suspending agent, a solubilizer, a stabilizer, an isotonizing agent, a preservative, an adsorption inhibitor, a surfactant, a diluent, an excipient, a pH adjuster, an analgesic agent, a buffering agent, an antioxidant, etc., if necessary depending on the administration method or formulation. Pharmaceutically acceptable carriers and formulations suitable for the present invention are described in detail in the literature [Remington's Pharmaceutical Sciences, the latest edition].

The cellular therapeutic agent or pharmaceutical composition according to an embodiment may be prepared in a unit dose form by formulation using a pharmaceutically acceptable carrier and/or excipient or may be prepared by incorporating into a multi-dose container, according to a method which can easily be performed by those skilled in the art to which the present invention belongs.

Additionally, the cellular therapeutic agent or pharmaceutical composition may be administered by any device in which the transdifferentiated chondrocyte (i.e., the active ingredient) can move to the target lesion. The cellular therapeutic agent or pharmaceutical composition according to an embodiment may contain a therapeutically effective amount of transdifferentiated chondrocytes for the treatment of diseases. As used herein, the term "therapeutically effective amount" refers to an amount of an active ingredient or a pharmaceutical composition that induces a biological or medical response in a tissue system, animals, or humans, as contemplated by researchers, veterinarians, medical doctors or other clinical studies, and it includes an amount that induces the alleviation of the symptoms of the disease or disorder being treated. It will be apparent to those skilled in the art that the dose of the transdifferentiated chondrocytes contained in the cellular therapeutic agent or pharmaceutical composition of the present invention will vary according to the desired effect.

Accordingly, the dose of the transdifferentiated chondrocytes to be contained in the cellular therapeutic agent or pharmaceutical composition of the present invention can easily be determined by those skilled in the art, and can be adjusted according to various factors including type of disease, severity of disease, contents of other components contained in the composition, type of formulation, age, body weight, general health conditions, sex and diet of the patient, administration time, administration route and excretion rate of the composition, duration of treatment, drugs to be administered simultaneously, etc. The cellular therapeutic agent or pharmaceutical composition of the present invention according to an embodiment may be administered to an area where the treatment of cartilage damage disease is needed (cells, tissues, or organs), for example, the joint cavity where damaged cartilage is present.

It is important to include the amount by which all of the above factors can be taken into account and the maximum effect can be obtained in a minimum amount without side effects. For example, the dose of the cellular therapeutic agent or pharmaceutical composition of the present invention according to an embodiment may be $1.0 \times 10^5$ cells/kg to $1.0 \times 10^9$ cells/kg (body weight), and more preferably, $1.0 \times 10^6$ cells/kg to $1.0 \times 10^8$ cells/kg (body weight). However, the dose may be variously prescribed based on factors such as method of formulation, method of administration, age, body weight, sex, pathological conditions, food, administration time, administration route, excretion rate, and responsiveness of the patient, and the dose may be appropriately adjusted by those skilled in the art considering these factors. The administration may be performed once, or twice or more within the clinically acceptable range of adverse effects, and the administration can also be administered to one site or two or more sites. Even for animals other than humans, the dose administered may be the same as that for humans per kg, or for example, the dose calculated in terms of volume ratio (e.g., average value) of ischemic organs (heart, etc.) between the animal of interest and humans, etc. may be administered. Examples of the subject animal to be treated according to the present invention may include humans, and other mammals of interest, and specifically include humans, monkeys, mice, rats, rabbits, sheep, cows, dogs, horses, pigs, etc.

The cellular therapeutic agent or pharmaceutical composition of the present invention according to an embodiment, in a specific embodiment, fibroblasts may be isolated from an individual and treated in vitro by the method according to the present invention, and the fibroblasts may be transdifferentiated into chondrocytes, and the chondrocytes may be used for ex vivo cell therapy for the prevention or treatment of diseases by transplanting the chondrocytes into a target lesion.

Hereinafter, the present invention will be described in more detail through Examples and Experimental Examples. However, the present invention is not limited to these Examples and Experimental Examples described below, but may be implemented in various other forms, the following Examples and Experimental Examples are provided so that the disclosure of the present invention is complete and that those skilled in the art fully understand the scope of the invention.

Example 1: Isolation of Fibroblasts from Various Tissues 1-1: Isolation of Fibroblasts from Skin Tissue The skin tissue of the forearm 3 cm away from the wrist of an adult human male was cleaned and disinfected with 70% isopropyl alcohol, and the disinfected site was subjected to local anesthesia with 1% lidocaine and the skin tissue was collected using a 2-mm punch, and the skin biopsy was further resected in 4 to 5 pieces, sterile T25 flasks were supplemented with glutamax, 2 mL of DMEM-F12 medium supplemented with 1% penicillin/streptomycin, 1% HEPES, 1% sodium pyruvate, and 20% heat-inactivated fetal bovine serum were dispensed, and once the flask floor is completely wet with the medium, the medium is removed, and the skin slices were carefully placed on the bottom of the medium, 0.5 mL of DMEM-F12 medium was added thereto, the flask was transferred to a cell incubator under the conditions of 5% $CO_2$ and 37° C., and then cultured for 3 days. The skin tissue can be collected from the earlobes where the peripheral nerves are less dense than the wrists, instead of the wrist region.

Then, the flask was observed daily and when the cells grew from the skin tissue, 1 mL of additional medium was carefully added to the flask. Once it was confirmed that fibroblasts were emerging from the original cell layer, the cells were treated with trypsin and transferred to a T75 flask.

1-2: Isolation of Fibroblasts from Muscle

Isolation of fibroblasts from muscle can be performed by the method of Agley et al. (Agley et al., *J. Cell Biol.*, 126(24): 5610-5625, 2013). Specifically, muscle tissue is obtained by needle biopsy with external suction from the muscle vestus lateralis of an adult male, visible fat or connective tissue is removed, muscle tissue is pulverized into smaller pieces of less than 1 $mm^3$ in a basal medium (PromoCell, Germany) supplemented with 2 mg/mL collagenase B (Roche, Germany) and 2 mg/mL of dipase II, and allowed to react for 1 hour while further pulverizing the muscle-derived cells at 15 minute intervals. The enzyme isolation is terminated by adding a growth medium (PromoCell, Germany) The cell suspension is passed through a 100 μm filter to remove muscle fiber debris and the filtered cells are centrifuged at 657×g for 6 minutes at 20° C.

1-3: Isolation of Fibroblasts from Ligaments

The isolation of fibroblasts from ligaments can be basically performed by a conventional method (Ge et al., *Cell Transplantation*, 14: 573-583, 2005). Specifically, the femoral and tibial inserts of the hind limb knee ligaments of a male New Zealand white rabbit (2.2 kg to 2.5 kg) are removed and then the synovial sheath and the periligamentous tissues are removed from the ligaments. After separating anterior cruciate ligament (ACL) and the medial collateral ligament (MCL), respectively, each ligament is carefully resected to a size of 1 mm×1 mm×1 mm, allowed to react by shaking in 5 mL of 0.25% collagenase (Gibco, USA) at 37° C. for 6 hours, and then washed twice with DMEM. Ligament cells isolated from ACL were suspended in DMEM (pH 7.4) supplemented with 10% FBS, penicillin (10,000 U/mL), streptomycin (10,000 U/mL), 2 mM L-glutamine in a T25 flask, cultured under the conditions of 37° C., 5% $CO_2$ at 3 day intervals, subcultured or part of it is frozen in liquid nitrogen, and stored in a −70° C. freezer until use.

1-4: Isolation of Fibroblasts from Gingival Tissue

The isolation of fibroblasts from gingival tissues can be performed by the method of Lim et al. (Lim, Hyun-Pil et al., *Journal of Korean Academy of Prosthodontics*, Vol. 44, No. 1, pp. 112-123, 2006). First, the healthy gingival tissues obtained after periodontal surgery are washed 5 times with phosphate buffered saline (PBS) containing antibiotics, and then placed in the Hank's balanced salt solution (Gibco, USA) containing 0.2% dispase (Gibco, USA) at 4° C. for 16 to 22 hours to isolate the epithelium and connective tissues. The obtained connective tissues are washed 5 times with PBS containing antibiotics and cut into a size of approximately 1 mm×1 mm×1 mm, 5 to 6 pieces of them were placed in a 35 mm culture dish in a 5% $CO_2$ cell incubator for 30 min without adding any medium, and once the tissues are attached to the culture dish, DMEM medium containing antibiotics and 10% fetal bovine serum were added thereto. The medium is replaced the next day and then replaced at 3 day intervals thereafter. When the cells grown from the tissues became dense, the cells are washed with PBS and 0.05% trypsin/0.53 mM EDTA (Gibco, USA) are added thereto and the cells were incubated at 37° C. in a 5% $CO_2$ incubator for 5 minutes. Once the cells are separated from the culture dish, DMEM medium (1 mL) containing 10% FBS is added thereto and the mixture is centrifuged at 1,000 rpm for 10 minutes, and only the cells are collected and subcultured.

Example 2: Cultivation of Micromass of Fibroblasts and Application of Electrical Stimulation The fibroblasts isolated in Example 1-1 were sufficiently cultured in a culture dish containing a culture liquid (DMEM-high glucose and 10% FBS) without any growth factor, the cell suspension (10 μL) at a concentration of $2 \times 10^7$ cells/mL was added to a 35 mm culture dish, and the culture dish was placed in an incubator (37° C., 5% $CO_2$) for 1 hour so as to form a micromass. Then, 3 mL of the culture liquid (DMEM-high glucose and 10% FBS) without any growth factor was added to the formed micromass and cultured while applying an electric field of 5 V/cm for 0.008 seconds at intervals of 5 times per second for 3 days using a multi-channel electric stimulator (C-Pace stimulator, Ion-Optics Co., MA, USA).

Comparative Example 1

The skin-derived fibroblasts isolated in Example 1-1 were sufficiently cultured in a culture dish, and the cell suspension (10 μL) at a concentration of $2 \times 10^7$ cells/mL was added to a 35 mm culture dish so as to perform micromass cultures. Then, 3 mL of the culture liquid (DMEM-high glucose and 10% FBS) without any growth factor was added to the formed micromass and the mixture was cultured for 3 days.

Comparative Example 2

The skin-derived fibroblasts isolated in Example 1-1 were sufficiently cultured in a culture dish, and the cell suspension (10 μL) at a concentration of $2 \times 10^7$ cells/mL was added to a 35 mm culture dish so as to perform micromass cultures. Then, 3 mL of the culture liquid (DMEM-high glucose and 10% FBS) containing TGF-β1 (10 ng/mL) was added to the formed micromass and the mixture was cultured for 3 days.

Experimental Example 1: Observation of Changes in Cell Morphology

In Examples above, it was demonstrated that skin cells were aggregated and effectively differentiated into chondrocytes by particular electrical stimulation conditions (electric field strength of 5 V/cm, application time of 8 ms, and frequency of 5 Hz). As shown in the above results, when the electric stimulation method according to one embodiment of the present invention is used, aggregation phenomena such as those occurring at the time of differentiation of cartilage in vivo were effectively induced (see the bottom of FIG. 1). In contrast, in Comparative Example 1 where no treatment was applied and Comparative Example 2 where growth factor TGF-β was treated, cell aggregation was not observed despite the lapse of time (see top and middle of FIG. 1).

Figure 2:
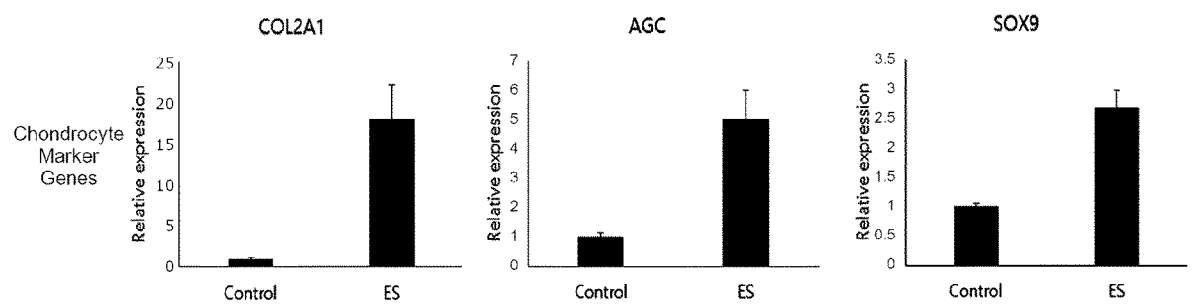
FIG. 2 represents the expression patterns of marker genes of chondrocytes and fibroblasts by electrical stimulation according to Comparative Example 1 (no treatment) and an embodiment of the present invention, and the results of real-time RT-PCR analysis are shown in graphs.
Figure 2:
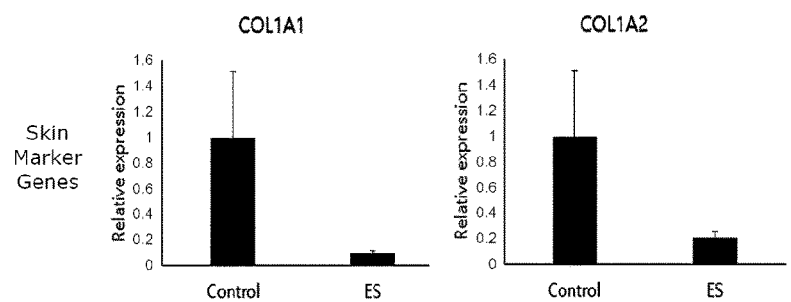

Experimental Example 2: Observation of Changes in Marker Gene Expression 2-1: Analysis of Real-Time RT-PCR Following the morphological observation of Experimental Example 1, the cells treated in Example 1 and Comparative Examples 1 and 2 were assayed with regard to the expression level of the cell phenotype marker gene by real-time RT-PCR, so as to confirm whether fibroblasts were actually transdifferentiated into chondrocytes by the method according to an embodiment of the present invention. Specifically, as a result of performing real-time RT-PCR using the primers shown in Table 1 below, the expression levels of skin cell marker genes (i.e., COL1A1 (approximately a 1/10 fold) and COL1A2 (approximately a 1/5 fold)) by the skin stimulation only (Example 1) were significantly reduced compared to the control group (Comparative Example 1), where no treatment was applied, and the TGF-β1 treated group, and the expression levels of chondrocyte marker genes (i.e., COL2A (approximately a 20 fold), AGC (approximately a 5 fold), and SOX9 (approximately a 9 fold)) were significantly increased (see FIG. 2).

TABLE 1

| Primer Name | Nucleic Acid Sequence (5'->3') | SEQ ID NO |
|---|---|---|
| COL1A1-F | GTCGAGGGCCAAGACGAAG | 1 |
| COL1A1-R | CAGATCACGTCATCGCACAAC | 2 |
| COL1A2-F | AATTGGAGCTGTTGGTAACGC | 3 |
| COL1A2-R | CACCAGTAAGGCCGTTTGC | 4 |
| COL2A1-F | GTGGAGCAGCAAGAGCAA | 5 |

TABLE 1 -continued

| Primer Name | Nucleic Acid Sequence (5'->3') | SEQ ID NO |
|---|---|---|
| COL2A1-R | TGTTGGGAGCCAGATTGT | 6 |
| AGC-F | AGGAGACAGAGGGACACGTC | 7 |
| AGC-R | TCCACTGGTAGTCTTGGGCAT | 8 |
| SOX9-F | TTCCGCGACGTGGACAT | 9 |
| SOX9-R | TCAAACTCGTTGACATCGAAGGT | 10 |
| GAPDH-F | ACCCAGAAGACTGTGGATGG | 11 |
| CAPDH-R | TTCTAGACGGCAGGTCAGGT | 12 |

2-2: Immunochemical Staining

Figure 3:
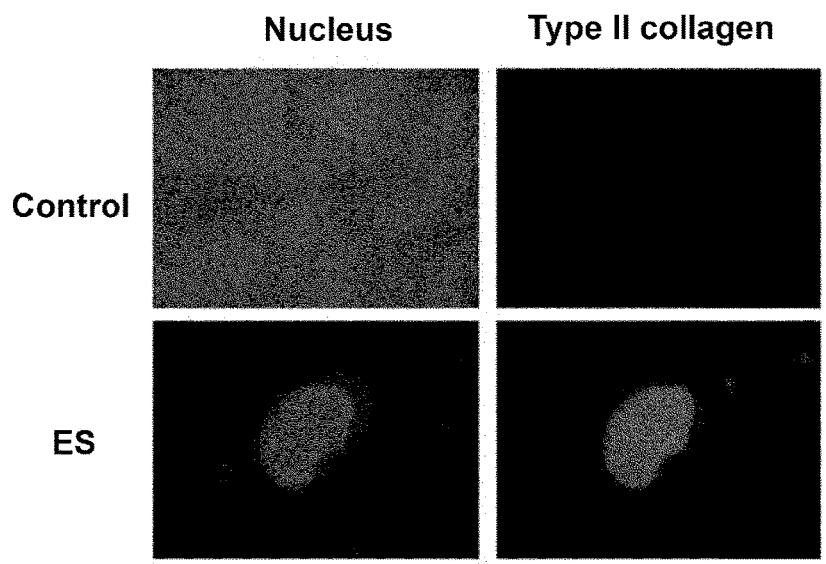
FIG. 3 represents fluorescence microscope images illustrating the results of immunocytochemistry analysis of type II collagen by electrical stimulation according to Comparative Example 1 and an embodiment of the present invention.

To further confirm the differentiation into chondrocytes, immunochemical analysis was performed on type II collagen with regard to adult fibroblasts (Comparative Example 1), where no treatment was applied, and fibroblasts (Example 2), where electrical stimulation was applied. Specifically, each cell was fixed with 4% paraformaldehyde at room temperature for 20 minutes, washed 3 times with PBS solution, and the resultant was subjected to a blocking reaction at room temperature for 1 hour using sheep serum (5%) containing Triton X-100 (0.3%). Then, the type II collagen antibodies produced in rabbits (1:500; EnoGene Biotech, New York, N.Y., USA) were reacted at 4° C. for 12 hours and washed 3 times with PBS solution. Then, secondary antibodies (1:200; Invitrogen), to which Alexa 488 was attached, were reacted at room temperature for 1 hour, washed 3 times with PBS containing 0.1% Triton X-100, and then the nuclei were stained with Hoechst 33258 (Dojindo, Tokyo, Japan). As a result, it was confirmed that type II collagen protein (i.e., the marker protein for differentiation of chondrocytes) was not detected in Comparative Example 1 (the control group), but type II collagen protein was distinctively expressed in the cells of Example 1 where electrical stimulation was applied (see FIG. 3). This result suggests that fibroblasts where electrical stimulation was applied were substantially transdifferentiated into chondrocytes, unlike skin-derived fibroblasts where no treatment was applied.

2-3: Alcian Blue Staining

Figure 4:
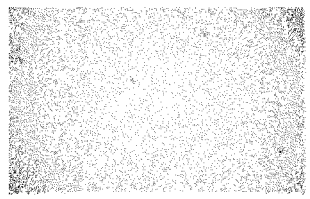
FIG. 4 represents optical microscope images illustrating the results of Alcian blue staining analysis for staining proteoglycan by electrical stimulation according to Comparative Example 1 and an embodiment of the present invention.
Figure 4:
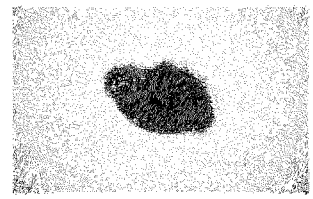

To further confirm the differentiation into chondrocytes, Alcian blue staining, which stains proteoglycan (i.e., a marker of chondrocytes), was performed with regard to adult fibroblasts (Comparative Example 1), where no treatment was applied, and fibroblasts (Example 2), where electrical stimulation was applied. Specifically, each cell was fixed with 4% paraformaldehyde at room temperature for 20 minutes, washed 3 times with PBS solution, Alcian blue solution (Nacalai tesque, INC., Japan: pH 2.5) was added thereto and the mixture was reacted at room temperature for 12 hours, washed 3 times with PBS solution and observed. As a result, as shown in FIG. 4, it was confirmed that in the case of Comparative Example 1 (the control group) where no electrical stimulation was applied there was almost no proteoglycan expression, whereas in the case of Example 2 where fibroblasts were cultured in a medium (DMEM/F12 and 10% FBS) for 3 days while applying only electrical stimulation thereto without introducing any growth factor, proteoglycan was distinctively expressed (see FIG. 4).

In the case of using the method according to an embodiment of the present invention, it can be seen that the transdifferentiation of fibroblasts into chondrocytes can be induced without using any gene therapy or growth factor within a very short period of 3 days. This method is simpler than the conventional two-step differentiation method where cells that have undergone differentiation are reprogrammed into stem cells and then differentiated into chondrocytes, and it is very useful in that it not only significantly reduces the possibility of cancer development due to the use of stem cells, but also minimizes unwanted side effects because it does not use gene therapy. Furthermore, since fibroblasts are easy to obtain from tissues such as skin, ligament, muscle, and periodontal tissue and are capable of proliferation in large quantities, it is possible to produce chondrocytes in a more economical and large-scale manner instead of mesenchymal stem cells, which are difficult to isolate and proliferate. Accordingly, the method according to an embodiment of the present invention can be very useful for the production of therapeutic agents for cartilage damage.

Although the present invention has been described with reference to the above Examples and Experimental Examples, these are provided for illustrative purposes only, and it will be understood by those skilled in the art that various modifications and equivalent other Examples and Experimental Examples are possible without departing from the scope of the present invention. Accordingly, the true scope of the present invention should be determined by the technical idea of the appended claims.

The invention claimed is:

1. A method for transdifferentiating fibroblasts into chondrocytes, comprising:
   forming a micromass of fibroblasts by culturing fibroblasts seeded a concentration of $1\times10^6$ cells/mL to $1\times10^8$ cells/mL; and
   applying an electrical stimulation to the micromass of fibroblasts while culturing the micromass of fibroblasts in a culture medium not containing growth factors,
   wherein at least a portion of the fibroblasts transdifferentiate into chondrocytes.

2. The method of claim 1, wherein the fibroblasts are derived from tendon, ligament, muscle, skin, periodontal tissue, cornea, cartilage, bone, blood vessel, small intestine, large intestine, or intervertebral disc.

3. The method of claim 1, wherein the electrical stimulation is applied by direct current.

4. The method of claim 1, wherein the electrical stimulation has an electric field strength of 0.1 V/cm to 100 V/cm.

5. The method of claim 1, wherein the electrical stimulation is applied at a cycle of 1 to 100 stimuli per second for 1 ms to 50 ms per stimulus.

6. The method of claim 1, wherein the electrical stimulation is performed for 1 to 10 days.

* * * * *

```
                        SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: COL1A1-F primer

<400> SEQUENCE: 1
gtcgagggcc aagacgaag                                                 19

<210> SEQ ID NO 2
<211> LENGTH: 21
<212> TYPE: DNA
<213> ORGANISM: Artificial Sequence
<220> FEATURE:
<223> OTHER INFORMATION: COL1A1-R primer

<400> SEQUENCE: 2
cagatcacgt catcgcacaa c                                              21

<210> SEQ ID NO 3
<211> LENGTH: 21
<212> TYPE: DNA
<213> ORGANISM: Artificial Sequence
<220> FEATURE:
<223> OTHER INFORMATION: COL1A2-F primer

<400> SEQUENCE: 3
aattggagct gttggtaacg c                                              21

<210> SEQ ID NO 4
<211> LENGTH: 19
<212> TYPE: DNA
<213> ORGANISM: Artificial Sequence
<220> FEATURE:
<223> OTHER INFORMATION: COL1A2-R primer

<400> SEQUENCE: 4
caccagtaag gccgtttgc                                                 19

<210> SEQ ID NO 5
<211> LENGTH: 18
<212> TYPE: DNA
<213> ORGANISM: Artificial Sequence
<220> FEATURE:
<223> OTHER INFORMATION: COL2A1-F primer

<400> SEQUENCE: 5
gtggagcagc aagagcaa                                                  18
```

<210> SEQ ID NO 6
<211> LENGTH: 18
<212> TYPE: DNA
<213> ORGANISM: Artificial Sequence
<220> FEATURE:
<223> OTHER INFORMATION: COL2A1-R primer

<400> SEQUENCE: 6
tgttgggagc cagattgt                                             18

<210> SEQ ID NO 7
<211> LENGTH: 20
<212> TYPE: DNA
<213> ORGANISM: Artificial Sequence
<220> FEATURE:
<223> OTHER INFORMATION: AGC-F primer

<400> SEQUENCE: 7
aggagacaga gggacacgtc                                           20

<210> SEQ ID NO 8
<211> LENGTH: 21
<212> TYPE: DNA
<213> ORGANISM: Artificial Sequence
<220> FEATURE:
<223> OTHER INFORMATION: AGC-R primer

<400> SEQUENCE: 8
tccactggta gtcttgggca t                                         21

<210> SEQ ID NO 9
<211> LENGTH: 17
<212> TYPE: DNA
<213> ORGANISM: Artificial Sequence
<220> FEATURE:
<223> OTHER INFORMATION: SOX9-F primer

<400> SEQUENCE: 9
ttccgcgacg tggacat                                              17

<210> SEQ ID NO 10
<211> LENGTH: 23
<212> TYPE: DNA
<213> ORGANISM: Artificial Sequence
<220> FEATURE:
<223> OTHER INFORMATION: SOX9-R primer

<400> SEQUENCE: 10
tcaaactcgt tgacatcgaa ggt                                       23

<210> SEQ ID NO 11
<211> LENGTH: 20
<212> TYPE: DNA
<213> ORGANISM: Artificial Sequence
<220> FEATURE:
<223> OTHER INFORMATION: GAPDH-F primer

<400> SEQUENCE: 11
acccagaaga ctgtggatgg                                           20

<210> SEQ ID NO 12
<211> LENGTH: 20
<212> TYPE: DNA
<213> ORGANISM: Artificial Sequence
<220> FEATURE:

```
<223> OTHER INFORMATION: GAPDH-R primer

<400> SEQUENCE: 12
ttctagacgg caggtcaggt                                                 20
```